Figure 1:
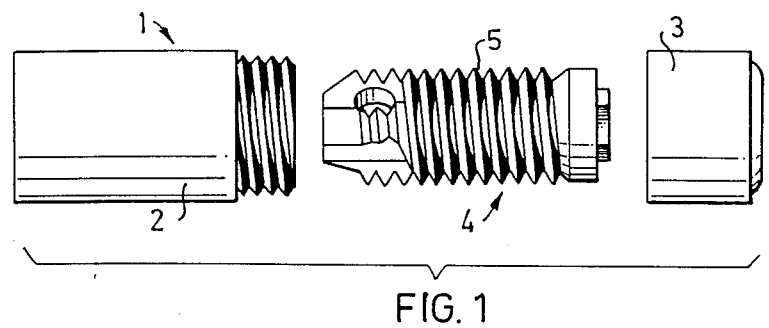

United States Patent [19]

Brånemark et al.

[11] Patent Number: 4,712,681
[45] Date of Patent: Dec. 15, 1987

[54] METHOD OF PACKAGING ARTIFICIAL IMPLANTS IN STERILE AND CONTAMINATION-FREE MANNER AND A PACKAGE THEREFOR

[76] Inventors: Per-Ingvar Brånemark, Ändergatan 3, S-431 39 Mölndal; Bengt Kasemo, Tjärkil 1400, S-464 00 Mellerud; Jukka Lausmaa, Pontus Wiknersgatan 3, S-411 32 Göteborg, all of Sweden

[21] Appl. No.: 813,355

[22] Filed: Dec. 26, 1985

[30] Foreign Application Priority Data

Dec. 27, 1984 [SE] Sweden .................... 8406592

[51] Int. Cl.⁴ .................... A61B 17/06; B65D 81/08
[52] U.S. Cl. .................... 206/438; 53/425; 53/449
[58] Field of Search .................... 53/167, 425, 449; 604/199; 128/419 P, 748; 206/438, 363, 524.6; 220/408, 415

[56] References Cited

U.S. PATENT DOCUMENTS

| | | | |
|---|---|---|---|
| 2,366,053 | 12/1944 | Putter | 206/363 X |
| 3,892,058 | 7/1975 | Komatsu et al. | 53/425 |
| 4,065,816 | 1/1978 | Sawyer | 53/449 X |
| 4,361,153 | 11/1982 | Slocum et al. | 128/419 P |
| 4,519,401 | 5/1985 | Ko et al. | 128/748 |
| 4,671,410 | 6/1987 | Hansson et al. | 206/524.6 |

Primary Examiner—Robert L. Spruill
Assistant Examiner—Steven P. Weihrouch
Attorney, Agent, or Firm—Armstrong, Nikaido, Marmelstein & Kubovcik

[57] ABSTRACT

The invention relates to a method of packaging artificial implants in a sterile and contamination-free manner, comprising applying the implant inside a closable capsule made of the same material as the implant, thereafter enclosing the capsule in a hermetically sealable outer casing and sterilizing the package thus produced, and also to a package for performing the method.

11 Claims, 2 Drawing Figures

METHOD OF PACKAGING ARTIFICIAL IMPLANTS IN STERILE AND CONTAMINATION-FREE MANNER AND A PACKAGE THEREFOR

The present invention relates to a method of packaging artificial implants in a sterile and contamination-free manner and a package therefor.

It is well known that the biocompatibility of an implant material is intimately associated with the surface properties of the material, i.e. the chemical composition, microstructure and so on of the surface layer. It is therefore of the utmost importance that the surface layer is carefully controlled and specified at atom level. Two implants manufactured initially from the same material can, for instance, acquire totally different biochemical properties depending on how the material is treated and the purification procedure employed when the implant is manufactured.

The method according to the present invention and the package used therefor can be generally employed for all types of artificial implants, instruments, etc. which can withstand sterilization temperatures. In the following the invention will be described as applied to titanium fixtures for implantation without, however, being limited thereto.

The high degree of biocompatibility of such titanium fixtures is intimately associated with the (oxide) surface formed at the manufacturing stage and subsequent treatment of these titanium fixtures. This special surface treatment is essential to ensure firm anchoring of the titanium fixture in the bone tissue when such fixtures are used, for instance, to provide attachment means for artificial teeth, dental bridges, prosthesis parts, etc. Since, therefore, the surface layer of the titanium fixture is of decisive significance for the implantation process aimed at, it must be guaranteed that this surface remains unaltered from manufacture to use.

Such titanium fixtures have previously been supplied in special boxes and then individually washed and sterilized prior to use, sterilization usually being performed in an autoclave. However, in practice it has been found that this known method has a number of drawbacks in that it is impractical for the user and especially that it is unsatisfactory from the cleanliness aspect. It has been found, for instance, that the surface layer of titanium fixtures stored and treated in this matter is altered in uncontrolled manner depending on the autoclave used for sterilization, the purity of the water, etc. In many cases major alteration in the surface layer of the implant can be observed which might jeopardize the implantation process.

There is therefore an acute need for a package for such titanium fixtures which guarantees that they are received by the user in a condition which will not jeopardize the subsequent implantation process. The demands placed on such a package are extremely high and are not fulfilled by any sterile package commercially available hitherto.

The object of the present invention is thus not only to fulfil the demands for sterility in conjunction with the artificial implants under consideration, but also to guarantee freedom from contamination right down to the atom/molecule level.

According to the invention it has now surprisingly proved possible to solve the problems described above and this is achieved in the method described in the introduction by applying the implant inside a closable capsule made of the same material as the implant, thereafter enclosing the capsule in a hermetically sealable outer casing and sterilizing the package thus produced.

According to a suitable embodiment of the method according to the invention, sterilization is performed for 2-4 hours at a temperature of 160°-180° C. and may suitably be performed by means of dry sterilization in air or by means of sterilization in an autoclave.

According to a suitable embodiment of the invention hermetically sealable metal foils or hermetically sealable glass wrappings are used for the outer casing.

The invention also comprises a package for sterile storage of artificial implants and this package is substantially characterised by an inner capsule to hold said implant, made of the same material as the implant, and a hermetically sealed outer casing surrounding said capsule.

Further characteristics of the invention are revealed by the features defined in the accompanying claims.

Figure 2:
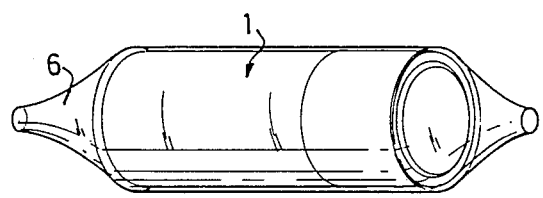

The invention will be described in more detail in the following with reference to a number of embodiments shown in the accompanying drawings in which, FIG. 1 shows a view of a closable capsule and FIG. 2 shows a view of a package according to the invention comprising an inner capsule and a hermetically sealed outer casing.

The capsule 1 shown in FIG. 1 consists of a cylindrical body 2 with screw-on lid 3. According to a preferred embodiment of the invention it is made of titanium. The titanium capsule 1 is designed to hold a titanium fixture 4. The titanium capsule 1 provides protection against mechanical damage and has the considerable advantage of ensuring that the titanium fixture 4 only comes into direct contact with titanium. The titanium capsule 1 shown in FIG. 1 is neither sterile nor gas-tight per se, however, and does not therefore protect the surface of the titanium fixture 5 from all types of impurities. According to the invention, therefore, the outer casing shown in FIG. 2 is used, here in the form of a glass ampoule which both maintains the sterility and protects the surface of the fixture 5 inside the titanium capsule 1 from impurities.

To achieve the sterile packaging of a titanium fixture according to the invention the following steps are taken:

1. The titanium fixture 4 is applied inside the titanium capsule 1. It is essential that the highest degree of cleanliness is observed in this step.

2. The titanium capsule 1 containing the titanium fixture 4 is enclosed in a tight outer casing 6 such as the glass ampoule shown in FIG. 2. The package thus obtained is sterilized by heating to 160°-180°C. for 2-4 hours. Alternatively a small quantity of water may be introduced into the capsule before it is sealed, in which case heating to autoclaving temperature is sufficient.

Before the package is broken when it is to be used, it should preferably be treated in an autoclave to sterilize its outer sides.

The outer casing used according to the invention should therefore permit vacuum-tight sealing to prevent any possible impurities from reaching the sensitive surfaces of the titanium fixture located in the titanium capsule. A vacuum-tight seal automatically more than fulfils the requirement of a sterile seal. Another requirement is that the material of which the outer casing is made should not emit any form of impurities at the time of sealing or sterilization.

The package manufactured according to the invention should withstand the pressure variations occuring at dry sterilization (0.7 atm overpressure), as well as sterilization in an autoclave (0.5 atm underpressure–1.5 atm overpressure). Furthermore, the package shall of course withstand any stress which may occur during transport. Finally, the package must be easy to open and have no sharp edges.

The following materials and sealing methods were tested to find a suitable outer casing for the invention:

1. Metal foils (preferably Cu or Al), sealed by compressing the material so that it cold flowed.
2. Glass ampoules sealed by means of a gas flame.

Continuous surface analysis was performed to check that the titanium samples enclosed in the various outer casings described above maintained the required standard of cleanliness. XPS (ESCA) was used to investigate the impurity content on the titanium surfaces and to determine the thickness of the oxide layer.

The capsules were tested for leakage (He-leakage tracing).

TEST AND RESULTS

Outer casing of metal

When metal foils of Cu or Al were used for the outer casing according to the invention, the seal was obtained by pressing the foils together to such an extent that they merged. The readiness of copper and of aluminium to cold flow increases noticeably if extremely pure material which has been annealed is used.

The advantage of an outer casing produced in this manner is that it is clean, i.e. no contaminants whatsoever are emitted when the material is heated. Thin foils must be used to fulfil the requirement of convenience in using the package and this may entail certain problems in obtaining a reliable and durable seal.

Glass ampoules

Glass ampoules were tested as outer casings, i.e. glass tubes sealed by means of a gas flame. Glass ampoules are frequently used within the pharmaceutical industry and are considered reliably tight. However, it was necessary to investigate whether impurities were formed during the sealing or sterilization processes, which could be deposited on the surface of the fixture. Two different types of glass were tested and two different gas mixtures for the flame used for the seal, in the following combinations:

A. Pyrex glass/coal gas+oxygen gas
B. Quartz glass (VYCOR)/coal gas+oxygen gas
C. Quartz glass (VYCOR)/hydrogen+oxygen gas.

TEST SERIES 1

In the first test series machined titanium samples were used which had been washed clean. To achieve the highest degree of cleanliness the glass tubes were ultrasound-washed in trichlorethylene (30 min) and ethanol (15 min). The glass tubes were dried with a hot fan. Before sealing, the glass tubes were heated to about 400° C. using a gas flame (without sample) in order to expel any impurities. The titanium samples were then enclosed in the washed glass tubes. After sealing, some of the packages were sterilized by heating to 185° C. for three hours, followed by treatment in an autoclave. In a first test series no inner titanium capsule was used in order to obtain a more sensitive test of any transfer of impurities to the titanium surfaces. A sample which had been neither packaged nor sterilized was used as reference. The titanium samples analyzed in the first test series, and their surface composition and the thickness of their oxide layer determined by XPS analysis are shown in Table 1.

All the samples, including the reference sample, included a number of different impurities. That the reference sample contained Na, Fe and Pb indicates that these impurities were acquired during preparation of the tests and therefore have no relevance to the packaging method. Two conclusions can with all certainty be drawn from these analyses: lyses:

When the samples were sealed and sterilized in pyrex, boron, probably in the form of $B_2O_3$, was sometimes observed to be deposited on the surface of the titanium. The boron comes from the glass, in which it is one of the main constituents. It is most probable that the boron is released at sealing of the ampoule, since the temperature at the sealing point exceeds the melting point (approx. 450° C.).

When sealing quartz glass with a hydrogen-oxygen flame this emission of boron is avoided but sometimes nitrogen could be observed in a chemical form which had not been observed earlier (N* in Table 2 on titanium samples). This nitrogen probably originates from nitrogen oxides $NO_X$ formed by oxidation of the nitrogen content in the air in the hot hydrogen-oxygen gas flame during sealing. Lower temperatures are required for sealing pyrex than for sealing quartz glass which explains the absence of $NO_X$ in the samples enclosed in pyrex. Neither boron nor $NO_X$ had been detected in the previous analysis of the implant surfaces, indicating that they are impurities and should be avoided until their effect on biocompatibility is known. Samples packaged and sterilized in pyrex have an oxide layer of normal thickness, whereas the samples sealed and sterilized in quartz have a thicker oxide coating. The latter is probably caused by water being formed in the ampoule during sealing with a hydrogen-oxygen gas flame.

TEST SERIES 2

In a second test series titanium samples were used which had been placed inside a titanium capsule in accordance with FIG. 1, before the titanium capsule was enclosed in an outer glass casing. To avoid as far as possible impurities from machining, electro-polished samples were used for this series. The washed titanium samples were enclosed in titanium capsules which were ultrasound-washed in trichlorethylene and ethanol. The titanium capsules had to be clean on the outside also and were therefore handled with tweezers and plastic gloves during the experiments. The glass tubes were cleaned as described earlier and sealed using coal gas +oxygen gas in all cases. The packages thus obtained were sterilized by dry sterilization and treatment in an autoclave. The analysis results of this test series are shown in Table 2.

The relatively high percentages of Cl and S in the reference samples are certainly a result of adsorption from the electrolyte used during electropolishing and can therefore be ignored. The source of the Sn is unknown. No boron was detected on the samples enclosed in pyrex, indicating that even an untight titanium capsule protects the surface of the sample against boron impurities. The boron oxide released during the sealing process is probably not volatile at the temperatures reached during sterilization and remains on the outside of the titanium capsule.

The package according to the invention was thus manufactured from the same material as the artificial implant. If, for instance, the capsule is to contain a titanium fixture, both the capsule and its lid should be made of titanium. If the capsule is to hold a stainless steel implant, the capsule and lid shall be made of stainless steel material and so on.

If a different material is used for the capsule and for the implant there is a risk that the material of the capsule may rub off onto the implant or that microscopic quantities of the capsule may be transferred to the surface of the implant by vaporization.

Some attempt to position the capsule should be aimed at, particularly if the outer casing is of glass. This can be achieved by arranging a resilient, corrugated strip of the same material as the implant between one short end of the capsule and the corresponding end of the ampoule or at both ends of the capsule.

The contents of the capsule are sterilized (free from contamination) after sealing by heating to 160°–180° C. This results in dry sterilization since the capsule is filled with air. Prior to clinical use, the outside of the capsule is sterilized in an autoclave together with instruments, etc.

If for some reason the implant is to be sterilized at a lower temperature than 160°–180° C. (or if a moist atmoshpere is desired) a small, specified quantity of water may be added before the capsule is sealed, in which case heating to autoclaving temperature is sufficient.

capsule in a hermetically sealable outer casing which is then hermetically sealed, and sterilizing the package thus produced, wherein said implant is removed from the casing and capsule prior to implantation.

2. A method according to claim 1, wherein the package is heated to between 160° and 180° C. for 2–4 hours in order to sterilize it.

3. A method according to claim 1 or 2, wherein hermetically sealable metal foils provide the outer casing.

4. A method according to claim 1 or 2, wherein hermetically sealable glass wrappings provide the outer casing.

5. A method according to claim 1 or 2, wherein the package is sterilized by means of dry sterilization in air.

6. A method according to claim 5, wherein the package is sterilized in an autoclave.

7. A package for sterile and comtamination-free storage of artificial implants, comprising an inner capsule to hold said implant and made of the same material as the implant, and a hermetically sealed outer casing surrounding said capsule, wherein said implant is removed from the casing and capsule prior to implantation.

8. A package according to claim 7, wherein the inner capsule is closable.

9. A package according to claim 7, wherein the outer casing consists of two metal foils sealed hermetically to each other.

10. A package according to claim 7, wherein the outer casing consists of a hermetically sealable glass

TABLE 1

Composition of elements in Ti samples packaged in glass ampoules (ESCA analysis)
Test series 1: Without inner Ti capsule

| Element | Reference (unpackaged, unsterilized) | Pyrex, coal gas + oxygen gas, sterilized (185° C., 3 h) | Pyrex, coal gas + oxygen gas, sterilized (185° C., 3 h) | Quartz glass, hydrogen + oxygen gas, unsterilized | Quartz glass, hydrogen + oxygen gas, sterilized (185° C., 3 h) | Quartz glass, hydrogen + oxygen gas, sterilized (185° C., 3 h) |
|---|---|---|---|---|---|---|
| Ti | 26 (34) | 33 (37) | 29 (35) | 30 (37) | 25 (32) | 28 (34) |
| O | 48 (63) | 52 (58) | 47 (58) | 52 (62) | 50 (65) | 54 (64) |
| C | 21 | 8.7 | 18 | 13.2 | 21 | 11 |
| N | 2.0 | 1.5 | 1.2 | 1.2 | 2.2 | 1.1 |
| N* | — | — | — | 2.6 | 3.0 | 3.4 |
| Cl | — | 0.8 (0.9) | — | — | — | 0.5 (0.6) |
| S | 0.4 (0.6) | — | 0.8 (1.0) | — | — | — |
| Ca | 0.3 (0.4) | 0.1 (0.2) | — | — | — | — |
| B | — | 3.4 (3.8) | 2.0 (2.4) | — | — | — |
| Na | 0.7 (0.9) | — | 2.0 (2.4) | — | — | — |
| Fe | 1.2 (1.5) | — | — | 0.7 (0.8) | 1.8 (2.4) | 1.3 (1.5) |
| Pb | 0.3 (0.4) | 0.3 (0.4) | 0.1 (0.2) | 0.1 (0.2) | 0.1 (0.2) | 0.04 (0.04) |
| Thickness of oxide layer | 24Å | 44Å | 40Å | 37Å | >50Å | >50Å |

All concentrations are given in atom %. The numbers in parentheses indicate concentrations obtained if C and N are ignored.

TABLE 2

Composition of elements in Ti samples packaged in glass ampoules (ESCA analysis)
Test series 2: With inner Ti capsule

| Element | Reference (unpackaged unsterilized) | Pyrex, unsealed Ti-capsule | Pyrex, sealed Ti-capsule | Quartz glass, unsealed Ti-capsule | Quartz glass sealed Ti-capsule |
|---|---|---|---|---|---|
| Ti | 18 (33) | 18 (32) | 21 (34) | 26 (38) | 18 (32) |
| O | 32 (59) | 36 (64) | 41 (64) | 41 (59) | 34 (62) |
| C | 43 | 40 | 34 | 28 | 42 |
| N | 2.2 | 3.3 | 2.3 | 1.9 | 2.5 |
| N* | — | — | — | 1.2 | — |
| Cl | 2.6 (4.8) | — | — | — | 0.8 (1.5) |
| S | 1.6 (3.0) | 2.2 (3.9) | 1.3 (2.0) | 1.9 (2.7) | 2.0 (3.6) |
| Sn | 0.3 (0.5) | — | — | — | 0.1 (0.3) |
| Cu | — | — | 0.2 (0.4) | — | — |
| Thickness of oxide layer | 50 Å | >50 Å | >50 Å | >50 Å | >50 Å |

All concentrations are given in atom %. The numbers in parentheses indicate concentrations obtained if C and N are ignored.

We claim:

1. A method of packaging artificial implants for sterile and contamination-free storage, comprising positioning the implant inside a closable capsule made of the same material as the implant, thereafter enclosing the container.

11. A package according to claim 10, wherein said glass container consists of pyrex glass.

* * * * *